United States Patent
Bózsik et al.

(10) Patent No.: US 12,247,243 B2
(45) Date of Patent: Mar. 11, 2025

(54) DIRECT DETECTION METHOD FOR TICK-BORNE INFECTIONS AND A CELL TECHNOLOGY MEDIUM FOR THE METHOD

(71) Applicant: LYME DIAGNOSTICS KFT., Budakalász (HU)

(72) Inventors: Béla Pál Bózsik, Budapest (HU); Béla Bózsik, Budapest (HU); András Pál Bózsik, Budakalász (HU)

(73) Assignee: LYME DIAGNOSTICS KFT., Budakalász (HU)

( * ) Notice: Subject to any disclaimer, the term of this patent is extended or adjusted under 35 U.S.C. 154(b) by 126 days.

(21) Appl. No.: 17/598,785

(22) PCT Filed: Mar. 18, 2020

(86) PCT No.: PCT/HU2020/000011
§ 371 (c)(1),
(2) Date: Sep. 27, 2021

(87) PCT Pub. No.: WO2020/194003
PCT Pub. Date: Oct. 1, 2020

(65) Prior Publication Data
US 2022/0162665 A1 May 26, 2022

(30) Foreign Application Priority Data
Mar. 28, 2019 (HU) .................... P1900099

(51) Int. Cl.
*C12Q 1/04* (2006.01)
*G01N 21/65* (2006.01)
*G01N 33/49* (2006.01)

(52) U.S. Cl.
CPC ............... *C12Q 1/04* (2013.01); *C12Q 1/045* (2013.01); *G01N 21/65* (2013.01); *G01N 33/491* (2013.01); *G01N 2333/20* (2013.01); *G01N 2333/43556* (2013.01)

(58) Field of Classification Search
None
See application file for complete search history.

(56) References Cited

U.S. PATENT DOCUMENTS

| | | | | |
|---|---|---|---|---|
| 6,689,577 | B1 * | 2/2004 | Bozsik | C12Q 1/04 435/31 |
| 10,613,084 | B2 * | 4/2020 | Middeveen | G01N 33/56911 |
| 2003/0235875 | A1 | 12/2003 | Whitaker et al. | |

FOREIGN PATENT DOCUMENTS

| | | | |
|---|---|---|---|
| EP | 2889382 | A1 | 7/2015 |
| HU | 220169 | B | 12/2000 |
| WO | 0049405 | A2 | 8/2000 |
| WO | 2016105479 | A1 | 6/2016 |

OTHER PUBLICATIONS

Matton et al. "Bovine Borreliosis: comparison of simple methods for detection of the spirochaete in the blood". Trop. Anim. Hlth Prod. 1990, 22, 147-152.*
"Quantitative Buffy Coat (QBC) Test", "Microbe Online", May 31, 2021, https://rnicrobeonline.com/quantitative-buffy-coat-qbc-test-principle-method-analysis/, Sep. 27, 2021.
Authorized Officer: Barz, Wolfgang, International Search Report and Written Opinion issued in counterpart PCT application No. PCT/HU2020/000011, Jun. 19, 2020, 11 pp.
Bilal Aslam et al., "Immune escape strategies of Borrelia burgdorferi," Future Microbiology, Sep. 15, 2017, ISSN 1746-0913, pp. 1219-1237, https://www.ncbi.nlm.nih.gov/pubmed/28972415.
C. Eldin et al., "Limitations of diagnostic tests for bacterial infections," Medecine et Maladies Infectieuses, Jan. 24, 2019, pp. 98-101, https://www.sciencedirect.com/science/article/pii/S0399077X18306784.
Dawn R. Clifton et al., "Regulation and expression of bba66 encoding an immunogenic infection-associated lipoprotein in Borrelia burgdorferi," "Molecular Microbiology", Jun. 1, 2006, doi: 10.1111/j.1365-2958.2006.05224.X, pp. 243-258, 61 (1), https://www.ncbi.nlm.nih.gov/pubmed/16824109.
Elsie M. Eugui et al., "Separation of erythrocytes infected with murine malaria parasites in metrizamide gradients", "Parasitology", Jan. 25, 1979, Cambridge University Press, pp. 267-275, 79, https://www.ncbi.nlm.nih.gov/pubmed/537838.
Eric Ponder, "The Relation Betwee Red Blood Cell Density and Corpuscular Hemoglobin Concentration", Apr. 2, 1942, pp. 333-338, http://www.jbc.org/content/144/2/333.full.pdf.
Jack D. Bissett et al., "Detection of Tickborne Relapsing Fever Spirochete, Austin, Texas, USA", "Emerging Infectious Diseases", Nov. 1, 2018, DOI: https:doi.org/eid2411.172033, pp. 2003-2009, vol. 24, No. 11, https://www.ncbi.nlm.nih.gov/pubmed/30160650.
James W. Jacobberger et al., "Analysis of Malaria Parasite Infected Blood by Flow Cytometry", "Cytometry", Jun. 28, 1983, pp. 4:228-237, https://www.ncbi.nlm.nih.gov/pubmed/6198130.

(Continued)

*Primary Examiner* — Vera Afremova
(74) *Attorney, Agent, or Firm* — MILLEN, WHITE, ZELANO & BRANIGAN, P.C.; Ryan R. Pool

(57) ABSTRACT

This invention relates to a method for the direct detection of tick-borne infections, wherein the human/animal body fluid sample, ideally blood sample to be examined is obtained directly on a specified amount of cell technology medium establishing a partially hostile (semi-hostile) environment, the sample and the cell technology medium are mixed, incubated and stored, if required, meanwhile, the cells and pathogens of the subject are in the semi-hostile environment, then corpuscles and pathogens are separated; a small amount of blood cells from the "buffy coat" layer and blood cells located a few cell layers beneath it are supplemented to and mixed with the gained plasma, the sample is concentrated and the test is finally performed to detect pathogens in the plasma and in blood cells.

The claimed matter covers cell technology medium applied and its application interesting methods.

11 Claims, No Drawings

(56) References Cited

OTHER PUBLICATIONS

Kate von Lackum et al., "Carbohydrate utilization by the Lyme borreliosis spirochete, Borrelia burgdorferi," "FEMS Microbiology Letters", Dec. 14, 2004, doi:10.1016/j.femsle.2004.12.002, pp. 173-179, vol. 243, Issue 1, https://acadernic.oup.com/femsle/article/243/1/173/434844.

Louis A. Magnarelli et al., "Early detection and persistence of antibodies to Borrelia burgdorferi in persons with Lyme disease.," Zentralbl Bakteriol Mikrobiol Hyg A., pp. 392-399, https://www.ncbi.nlm.nih.gov/pubmed/3296563 • Year: 1986.

Oliver Nolte, "Nucleic Acid Amplification Based Diagnostic of Lyme (Neuro-)borreliosis—Lost in the Jungle of Methods, Targets, and Assays?", "The Open Neurology Journal", Jul. 2, 2012, pp. 129-139, vol. 6.

Sambor Grygorczuk et al., "Assessment of the frequency of different Borrelia burgdorferi sensu lato species in patients with Lyme borreliosis from north-east Poland by studying preferential serologic response and DNA isolates," "Annals of Agricultural and Environmental Medicine 2013", Jan. 4, 2013, pp. 21-29, vol. 20, No. 1, https://www.ncbi.nlm.nih.gov/pubmed/23540208.

Wikipedia, "Phenol red", 4 pp., https://en.wikipedia.org/wiki/Phenol_red#/media/File:Phenol_red_pH_6,0_-_8,0.jpg, Sep. 27, 2021.

Willy Burgdorfer et al., "Lyme Disease—A Tick-Borne Spirochetosis?," "Science", Jun. 18, 1982, pp. 1317-1319, vol. 216, https://www.ncbi.nlm.nih.gov/pubmed/7043737.

\* cited by examiner

DIRECT DETECTION METHOD FOR TICK-BORNE INFECTIONS AND A CELL TECHNOLOGY MEDIUM FOR THE METHOD

The subject matter of the invention is a method for the direct identification of tick-borne infections from human or animal body fluids, more specifically from blood and cerebrospinal fluid; moreover, a cell technology medium for this method, capable of storing the body fluid to be tested and preserving blood cells and contagious organisms, more specifically bacteria, viruses and fungi.

It is well known that most frequent tick-borne diseases include Lyme disease, bartonellosis, babesiosis, anaplasmosis, mycoplasmosis, tick-borne encephalitis and in certain climates tick-borne relapsing fever, tick typhus, and so on.

Both direct and indirect methods are used for the detection of the aforementioned diseases. Whereas direct methods identify the pathogen itself, indirect methods confirm the infection via the detection of the host's response to the pathogen.

Numerous indirect methods have been developed to diagnose different infections, most of them are based on the immune response (serology: ELISA, Western blot, immunoblot) and lymphocyte transformation test (LTT) is also applied recently.

The disadvantage of these methods is that they can be inappropriate in certain situations [P. D. C. Eldin, "Limitations of diagnostic tests for bacterial infections,"*Médecine et Maladies Infectieuses*, 2019, https://www.sciencedirect-.com/science/article/pii/S0399077X18306784] as, like in Lyme disease, the immune response may be delayed, absent or hung up [N. M. K. M. F. S. M. Aslam B, "Immune escape strategies of *Borrelia burgdorferi*," *Future Microbiol.*, pp. 1219-1237, 2017 October, https://www.ncbi.nlm.nih.gov/pubmed/28972415]. Different infections have to be examined for the species and strain of the pathogen meaning more sampling or more tests performed on the same sample.

The principle problem of indirect methods is that the test is highly dependent of the immune response and the behaviour of the pathogen (modifications in its immunogenicity), such is the case with Lyme disease [N. C. H. J. N. A. C. J. Clifton DR, "Regulation and expression of bba66 encoding an immunogenic infection-associated lipoprotein in *Borrelia burgdorferi*," *Mol Microbiol.*, pp. 243-58., 2006, https://www.ncbi.nlm.nih.gov/pubmed/16824109] and these circumstances lead to uncertainty. It can be observed that the level of seropositivity required for diagnosis develops only in the later stages of the disease [S. M. J. M. F. K. Melby K, "Detection of serum antibodies against *Borrelia burgdorferi* with some commercially available serological tests.," *NIPH Ann.*, pp. 13(2):37-44, 1990 December, https://www.ncbi.nlm.nih.gov/pubmed/2093855]; and IgM-IgG transition is inhibited within the immune response [A. J. Magnarelli LA, "Early detection and persistence of antibodies to *Borrelia burgdorferi* in persons with Lyme disease," *Zentralbl Bakteriol Mikrobiol Hyg A.*, pp. 263(3):392-9, 1987, https://www.ncbi.nlm.nih.gov/pubmed/3296563]. As a conclusion, early detection cannot always be performed, thus postponing the administration of required therapy and deteriorating the chance of recovery.

Direct methods can also be applied to detect tick-borne diseases, as the primary and important location of pathogens is body fluid, principally blood.

The most frequent and oldest method is visual examination, consisting of microscopic examination of body fluids, nevertheless, more advanced methods are also available including Polymerase Chain Reaction (PCR). Direct methods are often preceded by a preparatory method, e.g. culturing, DNA extraction, cellular fragmentation or degradation, however, these methods are mostly preparatory steps and not substantive detection methods. The method and the cell technology medium covered by this invention can be applied in combination with other sample preparation methods (e.g. DNA extraction can be performed from the sample stored and prepared in accordance with this invention) and the sample can be freely utilized before the application of the test methods.

In spite of the aforementioned differences, both direct and indirect methods share a common feature that is typical for serological (indirect) and PCR (direct) methods as well, specifically the necessity of knowing the subdivision of the pathogen, a new subdivision or modified pathogen requires a new test method. It is essential, because, although different pathogens of the same species have common gene sequences and surface antigens, great variability can be observed between most of the distinct strains [L. D. Derdáková M, "Association of genetic variability within the *Borrelia burgdorferi* sensu lato with the ecology, epidemiology of Lyme borreliosis in Europe," *Ann Agric Environ Med*, pp. 12(2): 165-72, 2002, https://www.ncbi.nlm.nih.gov/pubmed/16457468]; [P. O. K. M. M. A. Z. J. D. J. Z.-S. W. P. S. Grygorczuk S, "Assessment of the frequency of different *Borrelia burgdorferi* sensu lato species in patients with Lyme borreliosis from north-east Poland by studying preferential serologic response and DNA isolates," *Ann Agric Environ Med*, 2013, https://www.ncbi.nlm.nib.gov/pubmed/23540208]. This is enough to trigger a different response, in which—due to the modification of surface antigens—the antibody that is produced during the immune response is not the same as the antibody to be measured by available tests (as a result, the serological response cannot be measured with the test) or the gene sequences of the pathogen does not match exactly the so called "primer" of the PCR test (as a result, DNA amplification cannot be initiated). To increase the sensitivity of the method and improve the PCR method itself, the application of a mixture of numerous primers matching almost all existent variants of gene sequences can be considered, however, the genetic variability and the possible multiple coding of the same nucleic acid in different sequences make the use of the so called degenerate primers obligatory in the case of the PCR method. The latter can often lead to false positive responses (deteriorating specificity), for example different gene sequences require different temperature for amplification and it is possible that the applied temperature is enough for the fusion of a sequence in the mixture meaning that the primer binds to the sequence and triggers amplification even if they do not match exactly. Thus, even with the above mentioned modifications, the PCR reaction cannot be considered a completely reliable method in the detection of pathogens [N. O, "Nucleic Acid Amplification Based Diagnostic of Lyme (Neuro-)borreliosis—Lost in the Jungle of Methods, Targets, and Assays?," *Open Neurol J*, p. 129-139, 2012; 6, https://www.ncbi.nlm-.nih.gov/pmc/articels/PMC3514706].

It is well known that tick-borne diseases were first identified visually with microscopic examination as unknown pathogens, so for example, *Borrelia burgdorferi* was first classified as a distinct pathogen after the microscopic analysis performed by Willy Burgdorfer and *Babesia* after the identification by Victor Babes [W. B. A. G. H. S. F. B. J. L. G. E. D. J. P. Burgdorfer, "Lyme Disease—a tick-borne spirochetosis?," *Science*, p. 216 (4552): 1317-9, 1982. June 18, https://www.ncbi.nlm.nib.gov/pubmed/7043737].

Although PCR reaction is more advanced, visual identification is the key element of diagnosis in the most critical cases even today (J. D. Bissett, S. Ledet, A. Krishnavajhala, B. A. Armstrong, A. Klioueva, C. Sexton, A. Replogle, M. E. Schriefer and J. E. Lopez, "Detection of Tickborne Relapsing Fever Spirochete, Austin, Tex., USA;" *Emerging Infectious Diseases.*, 2018, https://www.ncbi.nlm.nib.gov/pubmed/30160650). As a conclusion, visual analysis is suitable for the quite reliable identification of both novel species and visually unique existing species.

As science is constantly improving, many other direct methods have been developed and are being advanced currently, thus, novel methods are also expected to be applied (e.g. Raman spectroscopy (RS), Stimulated Raman Spectroscopy (SRS), FEMS, MALDI TOF Mass Spectrometry, Fourier Transform Mass Spectrometry (FTMS), Flow Injection Electrospray Ionization Mass Spectrometry (FI-ESI-MS), gene sequencing based on electromigration, Flow Cytometry (FCM), Pulsed-Field Gel Electrophoresis, Single Enzyme Amplified Fragment Length Polymorphism (SE-AFLP), biosensors, etc.). As a result, when referring to direct methods in the context of the invention it includes all examinations confirming the infection via the direct detection of the presence of the pathogen or a part of it (protein, genome, etc.).

It is therefore clear that direct methods are more advantageous due to their reliability, the faster availability of results and consequently, the earlier administration of treatment.

It is also known that indirect human or animal diagnostic examinations are predominantly performed on blood samples. After pathogen invasion immune response develops via the blood and the lymphatic system acting as a communication and transport medium, therefore, it is appropriate for the examination of the immune response. Blood samples are practical and can be easily utilized in the examinations as they contain sufficient amount of antibody or other cell or molecule characteristic for the specified immune response and remain usable during the days after sampling as well.

In the case of direct pathogen detection, a tissue, predominantly body fluid must be found, in which the number of pathogens or their components to be detected are present in a concentration adequate for the test.

Infected skin area can also be suitable for sampling in certain infections, however, expanding erythema (chronic erythema migrans—Erythema Chronicum Migrans, ECM) caused by Lyme disease and striae caused by Bartonellosis can only be observed in a relatively small proportion of patients. These symptoms of the skin have diagnostic significance alone, therefore, examination may only be required to confirm the diagnosis or to serve scientific purposes [E. R.-S. Maja Arnež, "The importance of the size of erythema migrans (EM) for diagnosis of Lyme borreliosis in Slovenian children," *Zdrav Vestn*, pp. 470-479, 2012, E. R.-S. Maja Arnež, "The importance of the size of erythema migrans (EM) for diagnosis of Lyme borreliosis in Slovenian children," *Zdrav Vestn*, pp. 470-479, 2012]. For this reason, microscopic examination of cultured, direct or stained biopsy skin samples have less importance in the routine diagnosis.

The same applies to cerebrospinal fluid that contains a significant number of pathogens in neuroborreliosis, however, sampling necessitates a serious invasive intervention. Therefore, these methods only have scientific significance, or they can only be applied in extraordinary cases.

It follows from the foregoing that the application of blood as body fluid is reasonable in direct methods, as well.

Taking into account the current scientific knowledge, there is a substantial demand to detect tick-borne pathogens invading the body via the blood circulation (or possibly live as parasites in blood cells) directly from blood.

As a conclusion, the purpose of the invention was to develop a method fulfilling this requirement and eliminating the indicated disadvantages resulting from the scientific knowledge.

The specification of the closest patent (patent number HU 220 169) to the current invention describes a reagent and a method for the microscopic detection of pathogens, especially spirochaetes from body fluids.

The referred patent specification offered an advantageous direct method and reagent in relation to the scientific knowledge at that time, however, the method and the reagent were only developed for the visual method among direct methods, therefore, its applicability was limited. The reagent was suitable to distinguish between disintegrated human cells, parts of corpuscles and Borrelias with the stiffening of human cell membrane, nevertheless, the excessive glucose amount of the applied reagent could lead to the dehydration and disintegration of human cells (higher osmotic pressure associated with higher glucose content results in water efflux from the cell). We found that more aspects regarding the preservation and storing of the body fluid, the importance of which has already been established, were not taken into consideration in this known method.

Therefore, one of the leading objectives of the current invention is to provide an improved direct detection method for tick-borne infections from human or animal body fluids, especially from blood or possibly cerebrospinal fluid.

Regarding tests, it should be kept in mind that tests tend to be performed on small amount of sample (5-20 microliters) and not necessarily close to the site or the time of sampling.

As a result, samples must be stored and preserved appropriately. Adequate cell technology medium can accomplish it. Experience has shown that the parallel preservation of blood cells (corpuscles) and bacteria in the blood or in the blood cells can be extremely difficult.

The second objective of the invention is therefore the development of an adequate cell technology medium.

It was recognised that it plays an important role in the procedure, which part of the sample the test substance originates from.

Our experiences have shown certain additional requirements necessary for performing reliable direct tests, as follows:

The sample or at least the pathogens within the sample should be preserved/nourished as analysis is performed neither at the site nor immediately at the time of sampling;

Bacteria causing infection should be concentrated from even 4-10 millilitres of blood sample, as in the light of experiences the amount of sample required for different methods (5-20 microlitres) does not contain sufficient number of pathogens to produce a positive result in all symptomatic patients in routine diagnostics by direct tests;

The development of disturbing factors should be inhibited (such as visually disturbing artefacts, DNA fragments, etc.).

In the light of the fact that the size and light scattering of bacteria make them not or barely detectable with normal light microscope without staining, the application of dark-field microscopy is reasonable, which is capable of detecting pathogens being one order of magnitude smaller in diameter or thickness.

False positive results should be eliminated, that is the development of misleading morphologies should be inhibited.

Pathogens with different, however stable morphology within the family or strain should be distinguished from other similar pathogens (e.g. *Borrelia-Treponema*, that is Lyme disease, relapsing fever and syphilis or *Babesia-Bartonella*-Malaria).

In the case of any methods other than the visual method the followings should be kept in mind.

The most effective way to examine a component of a pathogen, such as DNA or RNA is to store and/or nourish the pathogens themselves until the test is carried out.

Ideally, pathogens are selected and concentrated afterwards and degraded to appropriate components, if required, depending on the applied test.

The development of cell fragments, DNA fragments and other artefacts must also be inhibited; disturbing factors must be eliminated (e.g. relative decrease of human DNA amount).

An experienced professional in the field can realize that the easiest method to preserve pathogens and inhibit the development of degradation products is to make the sample itself more permanent. Nevertheless, there is no existing method that could safely be applied in every situation.

In relation to the invention, it was realized that the suspected pathogen is to be nourished and its motion ensured on one hand, whereas the whole sample is to be preserved and the motion of human/animal cells restricted on the other hand.

It was found that the restriction of the cell motion (human/animal) obtained from the subject decreases the nutrient demand of cells, thus, the amount of nutrients in the medium is sufficient for a longer period of time, excessive concentration of such is not required; moreover, according to another aspect excessive nutrient concentration (e.g. glucose) would lead to the shrinkage of human/animal cells.

It was also found that as a result of an appropriate but not optimal environment bacteria survive, but reproduce slower, preventing the consumption of great amounts of nutrition thus the sample remains stable for a longer period. Therefore, according to the invention a "semi-hostile" or partially hostile environment should be established during the storing of the sample for the bacteria.

The point of the invention is that the human/animal blood sample or other body fluid being tested is obtained on a specified amount of cell technology medium covered by the invention; the sample is then carefully mixed, incubated and stored for up to 2-3 weeks, meanwhile, the cells of the subject and the pathogens are being stored in a semi-hostile environment, then the blood cells and pathogens are finally separated; at this point of the procedure the sample is called "plasma" to which a small amount originating from the "buffy coat" layer lining the plasma and a small amount of blood cells (erythrocytes, leukocytes, thrombocytes and ghost cells) originating from a few cell-layers lower are mixed together with; the sample is concentrated and tested for the detection of intracellular (within blood cells) and intercellular pathogens in the plasma. It should be noted that blood cells containing intraerythrocytic and intraleukocytic pathogens are lighter, thus, they are located right under the buffy coat layer after low-speed centrifugation with 2000-4000 g, therefore, with proper technique they can be handled together with the plasma and identified within the same procedure.

Besides the finding regarding the tested part of the sample, the direct method covered by the invention is based on the other principal finding that stability and storage life can be established if cells and pathogens from the body fluid of the subject are stored in a semi-hostile environment. It is also important to put the sample directly in the cell technology medium (samples must not be obtained earlier and mixed ex post with different types of culture media, additives or reagents) also significant is the application of adequate proportion of sample and cell technology medium quantities.

The sample should ideally be prepared with dual centrifugation:

The separation of blood cells and pathogens is ideally performed with sedimentation, low-speed centrifugation or filtration, if required.

Concentration is ideally performed with high-speed centrifugation.

During the procedure, after the low-speed centrifugation (ideally 3000 g) of the mixture containing approximately the same amount of sample and cell technology fluid (e.g. 4 ml sample and 4 ml cell technology medium), a small amount (ideally 5-10 microliters) of the "buffy coat" layer and a few layers right beneath it consisting of erythrocytes and other blood cells should be added back and mixed to the sample and tested finally after fast-speed centrifugation (ideally with 15 000-20 000 g), this way both cellular infections in the blood (corpuscles) and extracellular bacteria within the plasma can be examined.

It is practical to preserve the whole sample containing both cells and pathogens. The separation of human cells and bacteria also becomes possible this way.

As indicated above, the storing of the whole sample requires an appropriate cell technology medium either for visual identification or other direct methods.

In the case of visual testing methods, it is appropriate to consider the following: as the size and the light scattering of the bacteria is such that they are not or hardly detectable with a normal light microscope without staining, the application of dark-field microscopy is reasonable, which is capable of detecting pathogens with one order of magnitude smaller in diameter or thickness.

As indicated above, the storing of the whole sample requires an appropriate cell technology medium either for visual identification or other direct methods.

In order to be suitable to detect all tick-borne infections the medium has to sustain both pathogens living in the plasma (*Borrelia, Mycoplasma*, tick-borne encephalitis virus) and blood cells (erythrocytes and leukocytes) as intracellular pathogens cause numerous diseases (*Bartonella, Babesia, Anaplasma*).

The cell technology medium (culture media) typically contains carbohydrate sources to nourish stored cells, therefore, it sustains their viability for a longer period than native or buffered blood (e.g. with EDTA). EDTA, the most frequently applied additive of blood sampling only plays role in the inhibition of blood coagulation and the deactivation of a DNA-degrading enzyme (DNase) within the blood, therefore it promotes the preservation of DNA.

It is known that *Borrelia* utilizes various carbohydrate sources, for that purpose, the cell technology medium covered by the current invention contains mannitol (a sugar alcohol derived from mannose by reduction that enters cells slower as it cannot pass membranes), glycerol and glucose.

*Borrelia* being responsible for the greatest proportion of bacteria content in the samples we intend to test can utilize the following nutrients [B. S. K von Lackum, "Carbohydrate utilization by the Lyme borreliosis spirochete, *Borrelia burgdorferi,*" *FEMS Microbiology Letters*, pp. Volume 243, Issue 1, Pages 173-179, February 2005, https://academic.oup.com/femsle/article/243/1/173/434844]: "Growth kinetic analyses of *Borrelia burgdorferi* indicated that this bacterium can utilize a limited number of carbon sources for energy: the monosaccharides glucose, mannose, and N-acetylglucosamine, the disaccharides maltose and chitobiose, and glycerol.

Glucose +
Maltose +
Mannose +
GlcNAc +
Chitobiose +
Glycerol +"

In details:

Glucose

The cell technology medium stores predominantly blood samples, the cell content of that consisting of mainly erythrocytes.

It is well known that erythrocytes utilize glucose slower due to the lack of mitochondria. As a result, a slower reaction is initiated within them. We assume that any kind of bacteria, e.g. *Borrelia* can consume up the glucose away from erythrocytes, leading to an inappropriately low concentration for the survival of cells, which can happen under 2000 mg/l concentration. Greater glucose concentration could also pose a problem because it can trigger the breeding of intraerythrocytic parasites leading to the "burst" of tested erythrocytes.

Excessive glucose concentration, such as 20 000 mg/l in the patent number HU 220 169 can result in the osmotic shrinkage of erythrocytes, which may lead to artefact formation. This was the reason for the previous unsuccessful attempts to sustain human/animal cells besides maintaining longer stability of bacteria.

Increased nutrient uptake was also observed in the presence of tumorous cells.

In order to sustain both pathogens in the plasma and cells in the presence of any kind of major carbohydrate-consumer, a novel cell technology medium had to be developed.

A cell technology medium used for culturing typically contains the following components (component types of the novel cell technology medium covered by the invention are underlined):

pH buffers: to set proper pH, pH value must be set precisely and controlled with pH indicators.

Inorganic salts: to maintain osmotic pressure and ion balance of membranes. Osmotic pressure cannot be maintained with sugars alone, as living organisms utilize them leading to great changes in the osmotic pressure.

Amino acids: principle components of cells. Essential amino acids are typically supplemented as living organisms cannot produce them on their own. Taking into consideration that the sample is a closed system, non-essential amino acids are also often supplemented to the cultures (the culture medium developed by us does not contain additional amino acids because it contains blood as amino acid source, moreover, RPMI growth medium as a compound contains amino acids as well).

Carbohydrates: the most important nutrient of living cells and the main factor in the creation of osmotic pressure.

Proteins and peptides are also typically used in growth media not containing serum. Its primary role is to bind excess substances, water, salts, fatty acids and to inhibit the destructive activity of enzymes.

Fatty acids and lipids are also typically supplemented to growth media not containing serum.

Vitamins and trace elements: essential for the vital functions of cells (RPMI growth medium contains it).

Antibiotics: rarely applied in order to prevent unwanted infections, e.g. bacterial or fungal superinfections. Additional antibiotics must not inhibit the growth of cultured cells.

Serum: complex nutrient, buffer and protective substance. 2-10% is typically supplemented to media, e.g. BSK medium.

The cell technology medium covered by the invention contains the following components: 125-200 mg/l Tetracaine, 1500-2000 mg/l Mannitol, 0.76-0.114 mg/l EGTA [Ethylenebis(oxyethylenenitrilo)tetraacetic acid], reasonably 0.60 mg/l Magnesium-chloride, 2000-4000 mg/l Caffeine-sodium benzoate (Coffeinum natrii benzoici), 75-105 mg/l Glycerol, ideally 10 000 mg/l Trisodium citrate and, if applicable, 1.00 mg/l Hoechst 33342 stain solution and 20-40 ml distilled water; the point of this solution is that in addition to the above mentioned components it contains 2500-2900 mg/l glucose and 0.8-1.2 ml/g Phenol Red sodium salt as stain indicator supplemented with RPMI 1640 growth medium to 100 ml.

Surprisingly, we found that low glucose level could sustain erythrocytes (prevent their shrinkage) and establish the survival of pathogens for up to 3 weeks as probably due to the above-mentioned reasons the nutrient consumption of blood cells in the sample was controlled. The same applied for tumorous cells.

The long stability of the sample is probably due to the fact that cells barely survive in a liquid characterised by high osmotic pressure. The applied Hoechst stain binds to intracellular DNA and partially inhibits its replication—in other words reproduction, however, it does not prevent the application of PCR reaction on the final sample in most of the cases. Consequently, bacterial reproduction proceeds at a minimal level, nutrients are not consumed for a long time, but living functions sustain at a minimum level. The application of other known mitotic inhibitors, such as Sodium benzoate can also be considered.

The cell technology medium covered by the invention contains at least one, occasionally two stains.

According to patent number HU 220 169 Hoechst stain is supplemented to the medium in order to perform fluorescence examination as it causes fluorescence of stained cells—unfortunately, the indicated concentration did not result in the fluorescence of examined cells, the amount should have been increased.

Phenol red stain is typically applied as a pH indicator however, its colour slightly differs in our cell technology medium from that being published, despite pH value 7.0-7.3, the colour of the liquid corresponded with pH value 8.0 (bright pink). https://en.wikipedia.org/wiki/Phenol_red#/media/File: Phenol_red_pH 6,0_-_8,0.jpg We found, based on our detailed analysis and experience, that minor modification of the composition and the supplementation of Phenol Red stain, the stain has become sensitive to decomposition or denaturation processes of the medium as well, not only to the changes in pH value. It was observed and confirmed with experiments that the medium with this modified constitution changes its colour, if:

Frost damage occurred or the temperature exceeded 36° C.;

The medium was exposed to air (i.e. the sample was exposed to oxygen meaning an imperfect sealing of the container or syringe) even in 1-2 days.

The pH of the medium changed due to infection (every living organism modifies the pH value of its environment due to the consumption of nutrients, the production of chemicals and the modification of surrounding ionic balance).

In the cell technology medium covered by the invention this stain becomes more sensitive to changes in the environment and thus changes its colour.

The cell technology medium covered by the invention is suitable to preserve blood and pathogens within that, however, the sample must be prepared in accordance with the applied testing method to achieve the best possible result.

Suitable elements to be examined must be separated or signed in order to be selected. For that purpose, the cell technology medium can occasionally contain fluorescent stain, however, the preparatory method introduced in the invention is principally applied during the procedure covered by the invention.

The preparation is based on gravity, i.e. the differences in relative density and hydrodynamic characteristic of blood cells within the sample.

Tick-borne infections can be classified into 3 groups: pathogens located freely in the blood, parasites of erythrocytes and parasites of leukocytes. As indicated below, the possibility to detect all three types of infection required inventive activity.

After the first centrifugation the supernatant is used during the further steps in the procedure covered by the invention number HU 220 169, the sediment is disposed (as described, "blood cells and pathogens are separated"). It means that the sample was tested without blood cells (corpuscles) in the specified procedure. It limits the area of use, as the occurrence of pathogens is only examined in the remaining fluid that is in fact plasma without blood cells. Therefore, only extracellular pathogens visible with light microscope could be detected.

The previous method recommended to put the reagent to the sample and shake them afterwards.

Nevertheless, it was observed that if blood or any other body fluid is obtained in any kind of container, artefact formation indicating blood cell damage and blood coagulation almost immediately begins. The shaking of the sample and the reagent after sampling can lead to the same process. This phenomenon is particularly significant in the presence of heparin-type anticoagulants, making morphologic examinations impossible, moreover, failing to prevent cell damage. The application of EDTA has numerous detrimental effects as well during the microscopic examinations of native samples, therefore, it may prevent the performance of extended examinations.

According to the invention the sample is obtained directly on the culture medium and mixed with it immediately and carefully, thus, the stability of the sample increases, blood coagulation is blocked, it becomes difficult to misidentify the projections of platelets as spirochetes and a minimal amount of artefact is formed.

The proportion of the cell technology medium and the sample is determined to be approximately equal, for example 4 ml sample is obtained on 4 ml cell technology medium, as it improves further stability, due to the greater amount of culture medium being present per a unit of the sample.

It is well known that centrifuging separates body cells and other parts in body fluids based on their density. Centrifuging is also applied to produce plasma with the removal of all corpuscles, cells from the liquid fraction.

Nevertheless, the cell technology medium covered by this invention blocks the motion of human cells, therefore centrifuging produces a more precise gradient (distribution by density) than without the cell technology fluid.

Within this gradient our hypothesis was the following: healthy erythrocytes have the highest density among all cells in the sample obtained on this cell technology medium, therefore, they are located at the bottom of the sample. Erythrocytes contain haemoglobin that is a large molecule occurring in high concentration, however, they do not have nucleus (that is the reason for calling them "bodies" instead of cells in Hungarian). (see the following article that recommends centrifuging to determine haemoglobin concentration: http://www.jbc.org/content/144/2/333.full.pdf). Intraerythrocytic haemoglobin concentration can also change within the same sample, mostly if something with lower density enters the erythrocyte. It typically occurs during intracellular infections, when bacteria infecting erythrocytes modify the average density of the cell. We realized that these cells with lower density are located at the top of the erythrocyte layer, at the lining between the plasma and the sediment, as they are lighter than healthy erythrocytes.

Moreover, leukocytes have lower density than erythrocytes as well, therefore, they are also located at the lining between the plasma and the sediment. After centrifuging with an objective of diagnosing, thrombocytes floating in the plasma are also located at the surface of the erythrocyte mass, forming a layer with leukocytes (leukocytes+thrombocytes) that is known in literature as the "buffy coat".

As a summary, the top-down order is the following: plasma with bacteria, thrombocytes, leukocytes, infected erythrocytes and healthy erythrocytes.

We discovered that—as a support of our theory—after careful removal of the plasma from the top of the gradient, careful mixing of the "buffy coat" and the critical layer beneath it (sub-buffy-coat) and obtaining sample therefrom, erythrocytes and leukocytes infected by parasites occur in the sample in up to a hundredfold or thousandfold concentration compared to their normal concentration. It means a new method in the diagnosis of tick-borne Bartonellosis, Babesiosis and Anaplasmosis. A greater amount of sample (e.g. 4 ml) was applied in the case of these infections as well, because blood cells infected with these pathogens typically occur in a low concentration.

During the procedure covered by the invention a small portion of those erythrocytes is mixed to the plasma that are located at the lining of the plasma and the sediment representing a higher proportion of cells with lower density, meaning they are infected; this mixed sample is then concentrated with very high-speed centrifugation, applying 15 000-20 000 g (ideally 20 000 g) thus making it possible to find—in the concentrated sample —, extracellular pathogens in the plasma as well, besides infected blood cells.

Although the expression "buffy coat" is relatively well-known in literature, no information can be found on the fact that mixing a small amount of the buffy coat and the cells located 1-2 cell-layers beneath it to the plasma, the test method would visualize infected leukocytes as in the case of the procedure covered by the invention.

Several publications can be found in literature on the separation of corpuscles, however, these focus on malaria infection in general. In this case it is sufficient to analyse the gradient developed in a thin tube due to the relatively great number of infected cells.

For instance, mature and immature erythrocytes infected with malaria are separated due to their density with the application of Percoll density-gradient separator [P. K. H. J. D. H. J W. Jacobberger, "Analysis of Malaria Parasite Infected Blood by Flow Cytometry'," *Cytometry*, pp. 4:228-237, 1983, https://www.ncbi.nlm.nih.gov/pubmed/6198130] or metrizamide [A. A. Eugui EM, "Separation of erythrocytes infected with murine malaria parasites in metrizamide gradients," *Parasitology*, pp. 79(2):267-75, 1979 October, https://www.ncbi.nlm.nih.gov/pubmed/537838] density-gradient.

The disadvantages of the above-mentioned methods include the necessity of the preliminary composition of the density-gradient (metrizamide has further disadvantages, among others it is a light-sensitive material with storing difficulties) and that they allow the examination of a small amount of sample only. Their performance is expensive, requires special expertise and is associated with a great chance of misinterpretation.

For the sake of completeness, we note that it is mentioned in the referred description of the metrizamide method that sucrose is not suitable for the separation of cells with gradient due to its high osmotic pressure. This conclusion cannot be applied for all types of sugars, as the current invention confirmed it.

A far more complicated test method found at the following link is also known in literature, in which the developed gradient is analysed with microscope. https://microbeonline.com/quantitative-buffy-coat-qbc-test-principle-method-analysis/.

In this case, the volume of the sample is much smaller, 55 microliters, that is a small fraction of the 4 ml value applied for example in our procedure. Thus, the known method is suitable to detect evident and severe acute infections, such as malaria, but not infections associated with a smaller proportion of infected erythrocytes (e.g. *Bartonella, Babesia*) or infections of leukocytes (e.g. *Anaplasma, Ehrlichia*).

The description of the "buffy coat" can be found in literature. The importance of the layer beneath it was also reported (called sub-buffy coat), erythrocytes infected with malaria are concentrated within it [A. A. Eugui EM, "Separation of erythrocytes infected with murine malaria parasites in metrizamide gradients," *Parasitology*, pp. 79(2):267-75, 1979 October, https://www.ncbi.nlm.nih.gov/pub_med/537838]. Nevertheless, no information can be found relating to the mixing of cells from the buffy coat and the sub-buffy coat layer with plasma and recentrifuging it, the resuspending of the sediment and the test performed based on the above.

It can be considered as a novel conclusion that a test performed after the mixture of equivalent amount of sample and cell technology medium (e.g. 4 ml sample+4 ml growth medium) had been centrifuged with low-speed, 2000-3000 g (ideally 3000 g), a small amount (ideally 5-10 microliter) from the buffy coat and the layer right beneath it containing a few corpuscles and erythrocytes had been re-mixed to the sample (plasma) and the mixture had been centrifuged with high-speed (ideally 15 000-20 000 g), can detect the infection of blood cells (corpuscles) beside free extracellular pathogens. These infected cells occur in the sample in a greater proportion than in the native blood, in the non-concentrated blood or in the sediment without plasma (concentrated blood cells).

According to the specification of the patent number HU 220 169, the test method is visual, specifically microscopic. Nevertheless, it can be easily realized that a traditional light microscope is not suitable for the detection of the indicated spirochaetes without staining or the modification of the microscope. Crossing the borders of spirochaetes causes only a minimum level of light bending (partially due to their thinness) and the resolution of the microscope is very close to the 0.1-0.3 µm thickness of spirochetes. Therefore, the application of a dark-field microscope is reasonable to visualize thinner structures without staining. This is the method performed in practice on the sample prepared according to the referred patent.

We observed that the detection of pathogens from the blood poses similar problems during several other test as well:

It can be a problem, if insufficient number of pathogens is present in the sample.

Pathogens and their composing proteins, DNA, etc. degrade in the sample even within 24 hours, if no additives are supplemented to the body fluid (native blood), or EDTA or heparin is applied for anticoagulation or for the inhibition of DNase enzyme activity that degrades DNA. Certain PCR tests require the examination of the sample within 24 hours even in these cases. It is difficult to select the fraction of blood to be examined, that is, to decide whether one is examining the pathogens in the serum or in the blood cells.

On the other hand, the procedure of the invention can be applied during completely different test methods, i.e. not only during microscopic examination but other, more modern direct test methods, in which the testing and the direct detection of pathogens or their characteristic parts must be performed.

The Followings are Examples of Such Methods without Limitation:

Signing with various, predominantly vital stains or immunocytological methods, in which monoclonal antibodies assist in the determination of the strain, characteristics, vital functions and even fine structure characteristics of the pathogen.

Polymerase chain reaction and its modifications, highlighting RT-PCR and local hybridisation, and molecular beacon the most appropriate method to detect one cell. In general, 25-100 nanograms of DNA is required to perform the test and it is almost impossible to achieve that level without the concentration of pathogens. Nevertheless, EDTA applied during PCR tests only partially inhibits DNase enzyme activity and do not preserve pathogens. It can be observed that PCR tests should practically be performed within 24 hours after sampling in order to achieve the best result, otherwise the chance of accurate measurement significantly decreases. We assumed and confirmed the hypothesis that the visible living state, motion and moreover the multiplying of pathogens in the above fluid indicate an intact DNA or RNA content. This was confirmed with the PCR test of samples stored in the cell technology medium of the invention.

Raman spectroscopy. Every molecule responds individually to being irradiated with visible light. This response modifies the wavelength of the irradiated light and this modification is characteristic for every molecule. It is evident that the preceding two requirements have to be fulfilled here as well for a successful detection: pathogens must survive, i.e. their characteristic molecules must remain intact and sufficient number of them must be present for a measurable response—one pathogen hiding behind a blood cell is insufficient. The Raman microscope is suitable to examine a small volume of sample (in the microliter order of magnitude) at the same time. This method is also boosted by the preservation and concentration of pathogens (it is truly well-known that methods based on Raman spectroscopy are suitable to detect cells, pathogens or molecules under microscope).

Other test methods are also available, however, the concentration and the intact state of pathogens are crucial factors in all of them. The same applies to human cells, for instance tumorous cells in human blood.

It has become evident that the method of the patent number HU 220 169 is only suitable to detect pathogens in the serum, whereas several infections affect blood cells, besides tick-borne Lyme borreliosis, *Babesia* and *Bartonella* affect erythrocytes, and *Anaplasma* and *Ehrlichia* are parasites of leukocytes. It can also be observed that intraerythrocytic pathogens (pathogens infecting erythrocytes) appear in leukocytes as well —as a cellular sign of the organism's fight against pathogens—and promote the indication of treatment.

The above-mentioned infections are transmitted by ticks as well.

The method of the invention has been proven to detect pathogens that could not have been detected with the previous method and it would not be theoretically possible either, as those pathogens occur in blood cells.

Another advantage of direct detection morphology method with dark-field microscopy is that families and strains of bacteria typically have constant extracellular and intracellular manifestation forms, their development stages represent the activity of the process and indicate treatment, and they possess common group characteristics, e.g. differ in the case of antibiotic sensitivity as groups if they are classified based on the shape of manifestation. Among Borrelias, the shorter *B. garinii* and its group is typically sensitive to penicillin, whereas strains in the *B. afzelii* group that are longer than the diameter of an erythrocyte are barely affected by penicillin however, doxycycline is extremely effective against them.

In contrast with morphologic tests, differences in the genetic characteristics of a great number of, sometimes more than a hundred species make the performance of species-specific tests difficult. As a conclusion, whereas morphologic methods are suitable to detect genetically different *Borrelia* strains, serologic and PCR test are not necessarily, which decreases the sensitivity of these methods.

Furthermore, identical components of completely different strains make PCR tests more complicated, for instance the similar genetic structure of the extracellular flagella of certain bacteria and the intracellular flagella of Spirochaetes make tests more difficult despite the application of preliminary adsorbents due to the known cross-reactions. Very similar genetic structure can disturb even PCR tests thus, a completely different strain or species could be identified as *Borrelia*. These problems decrease the specificity of serologic and PCR tests, i.e. they lead to false positive results.

The following examples represent the method of the invention, but without limiting the invention, the examples are given to provide better understanding:

EXAMPLE 1

The composition of the cell technology medium:

1.00 mg/l Hoechst 33342 stain solution, 5 mg/l Phenol Red sodium salt, 200 mg/l Tetracaine, 2000 mg/l Mannitol, 0.76 mg EGTA, 0.61 mg/l Magnesium chloride (containing 6 water crystalline hydrate), 4000 mg/l Caffeine, 10 000 mg/l Trisodium citrate, 2500 mg/l Glucose, 105 mg/l Glycerol (87%) and 30.00 ml distilled water and RPMI 1640 culture medium ad 100.00 ml

EXAMPLE 2

Basically, the components of example 1 are applied, but an exhaustive list on the components of the culture medium is also provided. Therefore, the composition is the following:

COMPOSITION OF THE CELL TECHNOLOGY MEDIUM 1. 200 mg/l Arginine, 2. 56.82 mg/l Asparagine (H2O), 3. 20.00 mg/l Aspartic acid, 4. 0.20 mg/l Biotin, 5. 0.005 mg/l Vitamin B12, 6. 59.00 mg/l Cysteine disodium, 7. 0.76 mg/l EGTA, 8. 15.00 mg/l Phenylalanine, 9. 5.00 mg/l Phenol Red, 10. 1.00 mg/l Folic acid, 11. 105 mg/l Glycerol (87%), 12. 2500 mg/l Glucose, 13. 20.00 mg/l Glutamic acid, 14. 300.00 mg/l Glutamine, 15. 1.00 mg/l Glutathione, 16. 10.00 mg/l Glycine, 17. 15.00 mg/l Histidine, 18. 20.00 mg/l Hydroxyproline, 19. 1.00 mg/l Hoechst 33342, 20. 35.00 mg/l Inositol, 21. 50.00 mg/l Isoleucine, 22. 0.25 mg/l Calcium pantothenate, 23. 70.00 mg/l Calcium nitrate [Ca(NO3)2 6×H2O], 24. 400 mg/l Potassium chloride, 25. 4000.00 mg/l Caffeine and sodium benzoate, 26. 3.00 mg/l Choline chloride, 27. 50.00 mg/l Leucine, 28. 40.00 mg/l Lysine, 29. 0.61 mg/l Magnesium chloride (6×H2O) (5 mM), 30. 100 mg/l Magnesium sulphate (7×H2O), 31. 2000.00 mg/l Mannitol, 32. 15.00 mg/l Methionine, 33. 6000.00 mg/l NaCl, 34. 2000.00 mg/l NaHCO3, 35. 800.00 mg/l Na2HPO4, 36. 1.00 mg/l Nicotinamide, 37. 1.00 mg/l p-Aminobenzoic acid, 38. 20.00 mg/l Proline, 39. 1.00 mg/l Pyridoxine, 40. 0.20 mg/l Riboflavin, 41. 30.00 mg/l Serine, 42. 200.00 mg/l Tetracaine, 43. 1.00 mg/l Thiamine, 44. 25.00 mg/l Tyrosine disodium salt, 45. 20.00 mg/l Threonine, 46. 10 000 mg/l Trisodium citrate, 47. 5.00 mg/l Tryptophan, 48. 20.00 mg/l Valine, 49. distilled water ad 1000.00 ml The following is an example for the procedure of the invention:

EXAMPLE 3—PROCEDURE

Maximum 5 ml human blood (4.00 ml) or other body fluid sample from a specific patient is obtained directly on 4 ml cell technology medium of the invention. The cell technology medium is filled in the test tube/container in advance and the sample is obtained on that. The sample is carefully mixed (turning the tube/container up and down carefully) and then incubated for 120 minutes. Then the sample is stored for up to 2-3 weeks. Dual centrifuging is performed afterwards. Firstly, the sample is centrifuged with 3000 g for 10 minutes. 4450 microliters of supernatant and 50 microlitres from the buffy coat and the critical layer beneath it are mixed. These are then concentrated with the application of centrifuging with 17 000 g on 15-25° C. for 10 minutes and the supernatant is discarded afterwards. The part of the 4 ml sample that is intended to be examined is in this way concentrated into 10 µl, containing the sediment of the whole blood sample, from which approximately 2 µl is examined with dark-field microscope.

EXAMPLE 4—PROCEDURE

Sampling and sample preparation are the same as in example 3. Nevertheless, after high-speed centrifuging the sediment is resuspended in 50 µl supernatant and tested with PCR. We note that the optional Hoechst stain is not always supplemented to the cell culture medium in the case of PCR test, as it may inhibit the performance of certain PCR kits. Compatibility with kits must be checked in advance.

EXAMPLE 5—PROCEDURE

Sampling and sample preparation are the same as in example 3. Nevertheless, after high-speed centrifuging the sediment is resuspended in 5-10 µl supernatant and examined with Raman microscopy. The Raman microscope stimulates the concentrated sample with wavelengths characteristic for pathogens and components found in the sample and records the individually modified wavelength of the light. Special methods may be required for the amplification of the signal.

EXAMPLE 6—SAMPLE STORAGE

The cell technology medium of the invention is suitable to maintain a human or animal sample in a similar condition as it was at the moment of sampling with respect to corpuscles (blood cells), other cells or microbial flora present in the blood or in the corpuscles, so that the testing can be performed within the following 2-3 weeks. The fact that the examination of tumorous cells was also possible, supports this statement. The sample is obtained directly on the medium, in equivalent proportion, reasonably, obtaining 4 ml blood on 4 ml cell technology medium. For any intended examination on the sample, sample preparation must be performed according to the intended examination and the 4+4 ml sample must be handled as a native sample. The applied test can involve any kind of test method and affect any components of the sample including blood cells, pathogens or damaged cells. During certain procedures, in which sample concentration is relevant (e.g. number of blood cells in a unit of volume), it must be taken into consideration that the sample was diluted to double volume with the cell technology medium.

The invention claimed is:

1. A method for detecting tick-borne infections in human/animal body fluid of a subject, the human/animal body fluid comprising a blood sample containing plasma and blood cells, the method comprising the steps of:
   adding the blood sample directly into a specified amount of cell technology medium establishing a partially hostile environment for any pathogens infecting the plasma and any pathogens infecting the blood cells, due to the cell technology medium's low-level antibiotic or preservative content aiming at bacteriostatic effect and lowered sugar content;
   mixing the blood sample with the cell technology medium to provide a first mixed sample containing a mix of plasma and cell technology medium and the blood cells,
   centrifuging the first mixed sample at a speed of 2000 g-4000 g for at least 10 minutes, thereby obtaining the mix of plasma and cell technology medium, the blood cells, and a separating layer between the mix of plasma and cell technology medium, and the blood cells, wherein the separating layer comprises a "buffy coat" layer that contains blood cells;
   removing the mix of the plasma and cell technology medium from the blood cells and the buffy coat layer;
   mixing part of the blood cells from the "buffy coat" layer and the blood cells located a few cell layers beneath the buffy coat layer with the mix of the plasma and cell technology medium, thereby obtaining a second mixed sample;
   concentrating the second mixed sample at a speed of 15000-20000g for 10 minutes, resulting in a sedimented sample; and
   testing to detect pathogens in the sedimented sample, including the any pathogens infecting the plasma and sedimented therefrom and the any infected blood cells sedimented therefrom, which blood cells contain pathogens infecting the blood cells.

2. The method of claim 1, wherein the step of adding is performed by placing the blood sample directly on the cell technology medium and the step of mixing the blood sample with the cell technology medium is performed by carefully turning the cell technology medium and the added sample up and down.

3. The method of claim 1, wherein the volume of the blood sample added directly into the specified amount of cell technology medium and the volume of the cell technology medium are approximately equal.

4. The method of claim 1, wherein the step of centrifuging is performed at a low-speed of 3000 g-4000 g for at least 10 minutes, wherein the blood cells located the few cell layers beneath the buffy coat layer comprise erythrocytes, wherein the step of mixing with the mix of the plasma and cell technology medium comprises 5-10 microliters of the "buffy coat" layer and of the erythrocytes.

5. The method of claim 1, wherein for a volume of 100 ml of the cell technology medium, the cell technology medium has a composition that contains: 125-200 mg/l Tetracaine, 1500-2000 mg/l Mannitol, 0.76-0.114 mg/l EGTA [Ethylenebis(oxyethylenenitrilo)tetraacetic acid], 0.60 mg/l Magnesium chloride, 2000-4000 mg/l Caffeine-sodium benzoate (coffeinum natrii benzoici), 75-105 mg/l Glycerol, 10000 mg/l Trisodium citrate, 2500-2900 mg/l Glucose, 0.8-1.2 mg/l Phenol Red sodium salt stain, and 65-75 ml RPMI 1640 growth medium.

6. The method of claim 5, wherein the composition of the 100 ml volume of the cell technology medium further contains 1.00 mg/l Hoechst 33342 stain solution.

7. The method of claim 1, wherein the mixed sample containing the mix of the plasma and cell technology medium and the blood cells is incubated and stored for up to 3 weeks.

8. The method of claim 1, wherein the pathogen is *Borrelia burgdorferi*.

9. The method of claim 1, wherein the amount of blood sample is up to 5 ml of human blood or other body fluid and the amount of cell technology medium is 4 ml.

10. The method of claim 1, wherein sedimented sample comprises a 10 µl portion located directly below the buffy coat layer which is tested to detect pathogens.

11. The method of claim 1, wherein said testing to detect pathogens comprises examining at least 2 µl of the sedimented sample by dark-field microscope.

* * * * *